(12) United States Patent
Hober et al.

(10) Patent No.: US 8,916,689 B2
(45) Date of Patent: Dec. 23, 2014

(54) METHOD FOR LABELING OF COMPOUNDS

(75) Inventors: Sophia Hober, Stockholm (SE); Amelie Eriksson Karlstrom, Bromma (SE); Anna Konrad, Arsta (SE)

(73) Assignee: GE Health Bio-Sciences AB, Uppsala (SE)

( * ) Notice: Subject to any disclaimer, the term of this patent is extended or adjusted under 35 U.S.C. 154(b) by 0 days.

(21) Appl. No.: 13/820,201

(22) PCT Filed: Sep. 5, 2011

(86) PCT No.: PCT/SE2011/051065
§ 371 (c)(1),
(2), (4) Date: Mar. 1, 2013

(87) PCT Pub. No.: WO2012/033446
PCT Pub. Date: Mar. 15, 2012

(65) Prior Publication Data
US 2013/0184442 A1    Jul. 18, 2013

(30) Foreign Application Priority Data

Sep. 6, 2010   (SE) ...................................... 1050912
Apr. 15, 2011  (SE) ...................................... 1150325

(51) Int. Cl.
| C07K 14/315 | (2006.01) |
| G01N 33/53 | (2006.01) |
| G01N 33/533 | (2006.01) |
| G01N 33/532 | (2006.01) |

(52) U.S. Cl.
CPC ............ *G01N 33/533* (2013.01); *G01N 33/532* (2013.01)
USPC ...................................... 530/391.1; 530/324

(58) Field of Classification Search
None
See application file for complete search history.

(56) References Cited

U.S. PATENT DOCUMENTS

2003/0194370 A1* 10/2003 Stromgaard et al. ......... 424/1.11
2008/0064025 A1*  3/2008 Su ..................................... 435/5

FOREIGN PATENT DOCUMENTS

WO    WO 2009/136676    11/2009

OTHER PUBLICATIONS

Cedergren et al., protein Eng 6(4): 441-448, Jun. 1993.*
Denny, J., et al., Proc. Natl. Acad. Sci., 1984, vol. 81, pp. 5286-5290.
Schwartz, M., et al., Analytical Biochemistry, 1985, vol. 149, pp. 142-152.
Down, J., et al., Placenta, 1989, vol. 10, pp. 227-246.
Deisenhofer, J. (1981). "Crystallographic refinement and atomic models of a human Fc fragment and its complex with fragment B of protein A from *Staphylococcus aureus* at 2.9- and 2.8-Å resolution." Biochemistry 20: 2361-2370.
Dorman, G., et al., (2000). "Using photolabile ligands in drug discovery and development." Trends Biotechnol 18(2): 64-77.
Engfeldt, T., et al., (2005). "Chemical synthesis of triple-labelled three-helix bundle binding proteins for specific fluorescent detection of unlabelled protein." Chembiochem 6(6): 1043-50.
Gouda, H., et al., (1997). "NMR Study of the Interaction between the B Domain of Staphylococcal Protein A and the Fc Portion of Immunoglobulin G." Biochemistry 37: 129-136.
Gouda, H., et al., (1998). "NMR study of the interaction between the B domain of staphylococcal protein A and the Fc portion of immunoglobulin G." Biochemistry 37(1): 129-36.
Graille, M., et al., (2000). "Crystal stucture of a *Staphylococcus aureus* protein A domain complexed with the Fab fragment of a human IgM antibody: Structural basis for recognition of B-cell receptors and superantigen activity." Proc. Natl. Acad. Sci. 97: 5399-5404.
Jansson, B et al. (1998). "All individual domains of staphylococcal protein A show Fab binding." FEMS Imm. Med. Microbiol. 20: 69-78.
Jung, Y., et al., (2009). "Photoactivable antibody binding protein: site-selective and covalent coupling of antibody." Anal Chem 81(3): 936-42.
Kaiser, E., et al., (1970). "Color test for detection of free terminal amino groups in the solid-phase synthesis of peptides." Anal Biochem 34(2): 595-8.
Kawamura, A., et al., (2008). "Binding is not enough: flexibility is needed for photocrosslinking of Lck kinase by benzophenone photoligands." Bioorg Med Chem 16(19): 8824-9.
Nilsson, B., et al., (1987). "A synthetic IgG-binding domain based on staphylococcal protein A." Protein Eng 1(2): 107-13.
Stahl, S., et al., (1997). "The use of gene fusions to protein A and protein G in immunology and biotechnology." Pathol Biol (Paris) 45(1): 66-76.
Uhlen, M., et al., (1984). "Complete sequence of the staphylococcal gene encoding protein A." J. Biol. Chem. 259: 1695-1702.
Holm, L., et al., Journal of Biological Chemistry, vol. 284, No. 47, 2009, pp. 32906-32913.
European Search Report Dated Feb. 28, 2014 Issued on Corresponding EP Application No. 11823846.8.

* cited by examiner

*Primary Examiner* — Phuong Huynh

(57) ABSTRACT

The present invention relates to site-specific labeling of antibodies or fragments thereof with one or more reporter group(s) in a way that does not affect antigen binding. The method for labeling antibodies and/or fragments thereof, comprises the following steps a) providing an IgG binding protein, which comprises α-helix structures, with a photoactivatable group and at least one label; b) forming a mixture of said IgG binding protein and the antibodies and/or fragments to be labeled; and c) UV illuminating said mixture for site-specific labeling of said antibodies and/or fragments thereof. The IgG binding protein is preferably the Z domain of Protein A.

9 Claims, 6 Drawing Sheets

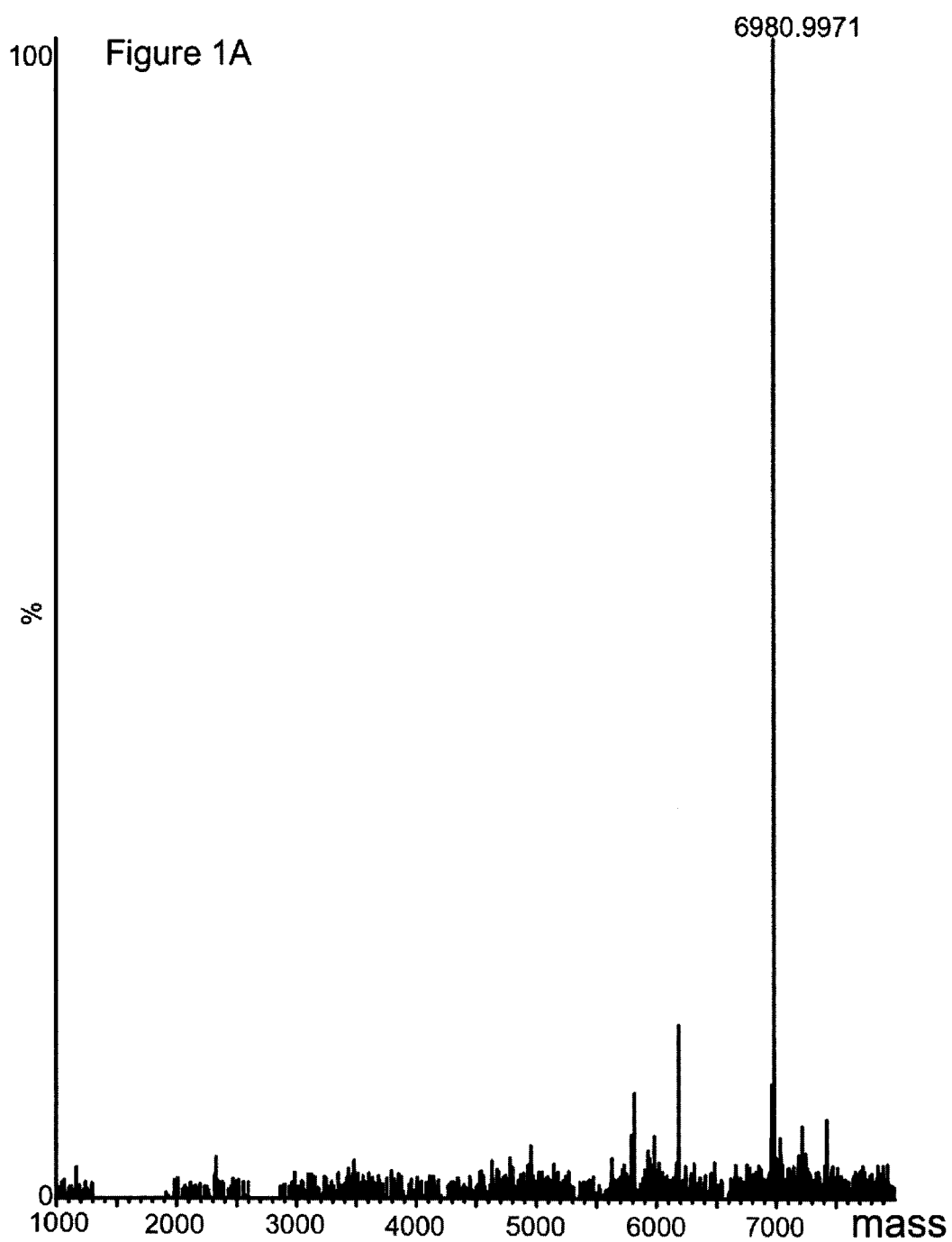

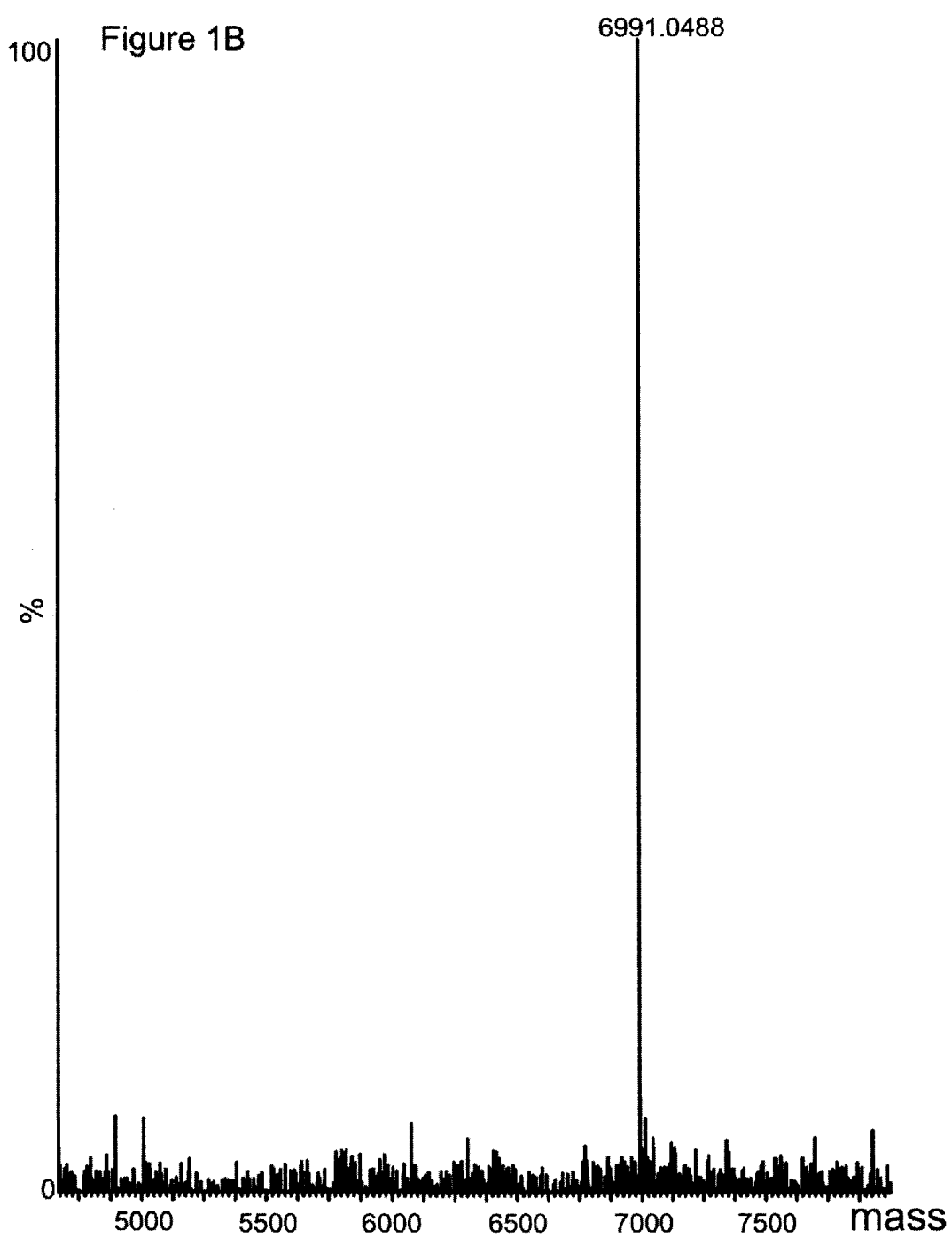

Figure 2
A)
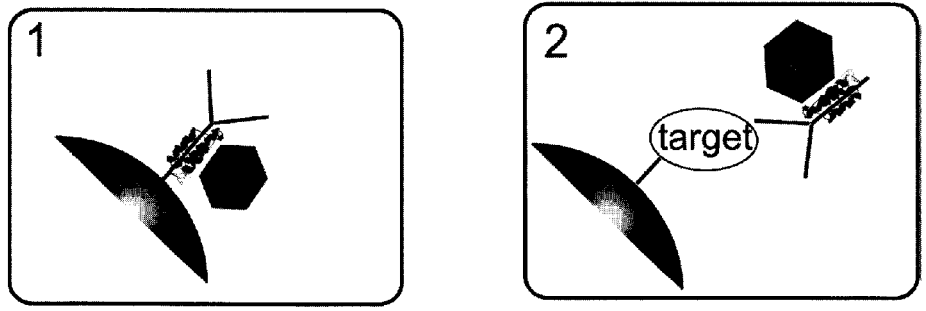
B)
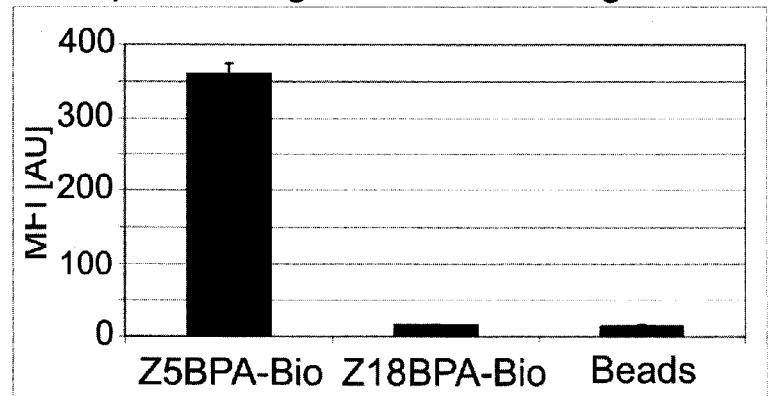
C)
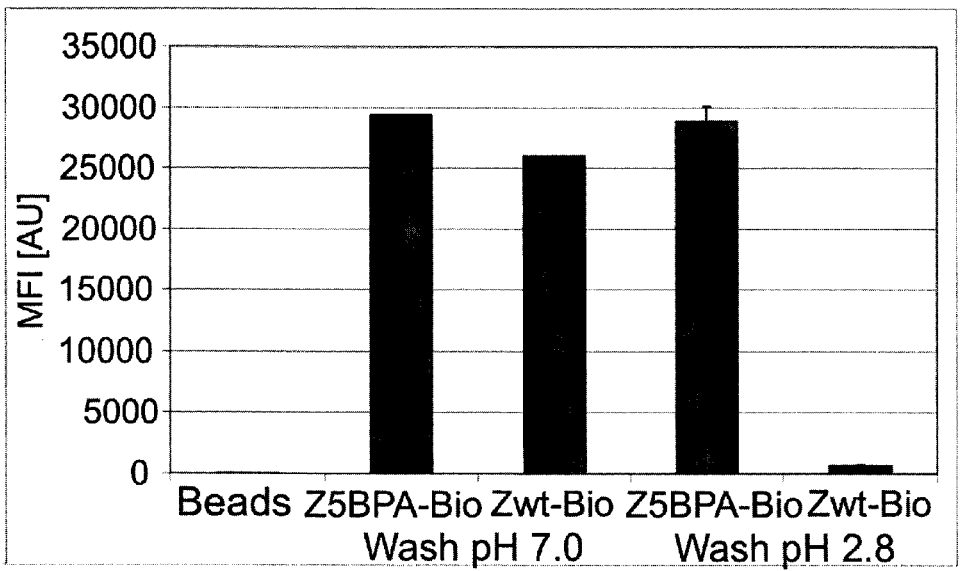

Figure 3
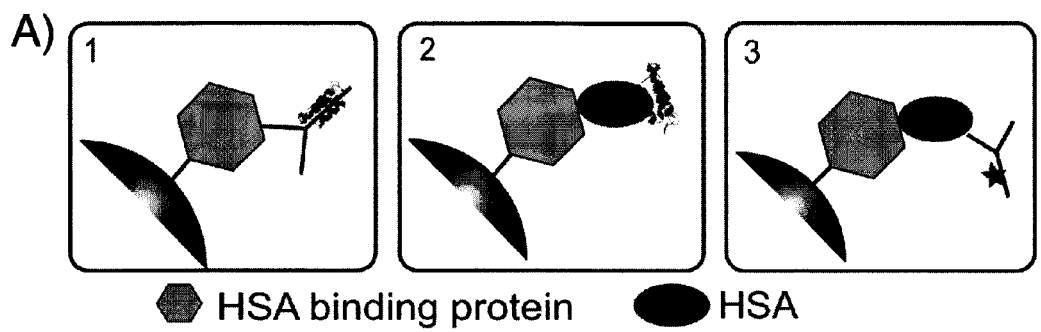
A)
HSA binding protein  ●HSA
B) Set-up according to number 1 in Figure 3 a.
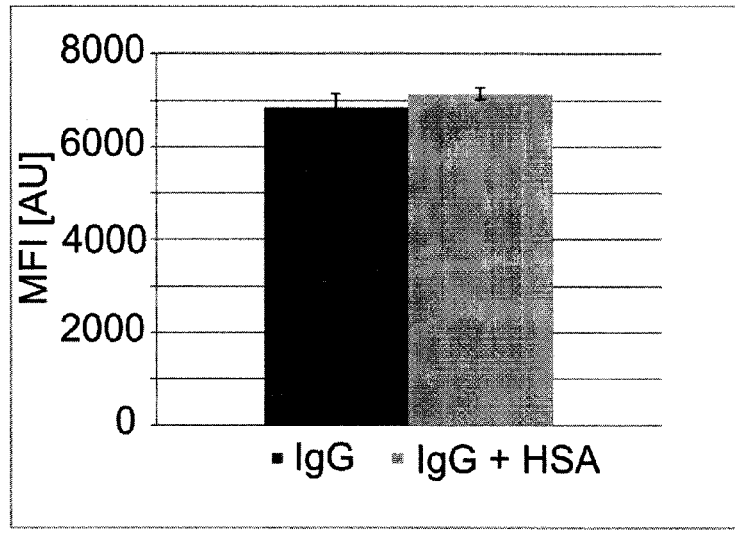
■ IgG  ■ IgG + HSA
C)
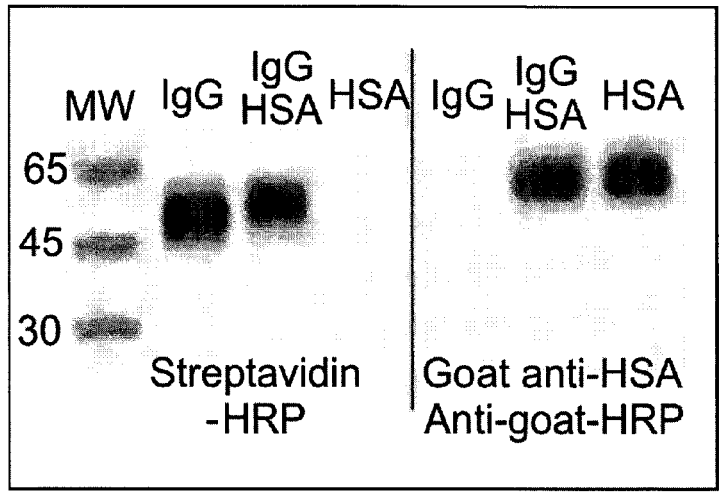

```
SEQUENCE LISTING

<160> NUMBER OF SEQ ID NOS: 2

<210> SEQ ID NO 1
<211> LENGTH: 58
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (5)..(5)
<223> OTHER INFORMATION: X = benzoylphenylalanine

<400> SEQUENCE: 1

Val Glu Asn Lys Xaa Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (18)..(18)
<223> OTHER INFORMATION: X = benzoylphenylalanine

<400> SEQUENCE: 2

Val Glu Asn Lys Phe Asn Lys Glu Gln Gln Asn Ala Phe Tyr Glu Ile
1               5                   10                  15

Leu Xaa Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

METHOD FOR LABELING OF COMPOUNDS

CROSS-REFERENCE TO RELATED APPLICATIONS

This application is a filing under 35 U.S.C. 371 of international application number PCT/SE2011/051065, filed Sep. 5, 2011, published on Mar. 15, 2012 as WO 2012/033446, which claims priority to Swedish patent application numbers 1050912-3 filed Sep. 6, 2010 and 1150325-7 filed Apr. 15, 2011.

FIELD OF THE INVENTION

The present invention relates to a method for labeling of compounds and compounds labeled by said method. More closely, the invention relates to site-specific labeling of antibodies or fragments thereof with one or more reporter group(s) in a way that does not affect antigen binding.

BACKGROUND OF THE INVENTION

Immunoglobulins, or antibodies, are a group of molecules that is extensively used as affinity reagents in many applications in research, clinical diagnostics and therapy. With the ability to bind their ligands with high affinity and in a selective manner they are of great importance, and are by far the most commonly used affinity reagents. As when employing any affinity reagent the method used for detection needs to be considered. The antibodies' excellent capacities to bind their ligands need to be combined with high selectivity in order to be of great use. As a consequence, techniques for labeling of antibodies necessarily need to be of high quality. To make detection of the antibody and its binding events possible, a reporter group is normally attached to the antibody. Methods most commonly used when conjugating reporter groups to the antibody are based on the exploration of amine- or carboxyl-groups in the protein for coupling. Another application that ordinarily takes advantage of the surface-exposed functional groups in the protein, is the immobilization to a solid support. When applying amine- or carboxyl-based chemistry, normally a high degree of labeling or immobilization is obtained, but unfortunately the binding site might be compromised since the control of level and location of the labeling/coupling is limited. This means that optimization of the protocol is needed for every antibody and every conjugation/immobilization. Hence, a method for labeling, where specific and controlled conjugation can be achieved, would be a great advantage. To obtain specific conjugation, molecules that have a natural, specific and defined binding to antibodies could be employed.

Several Ig-binding molecules have been reported in literature. Among these, staphylococcal protein A (SpA), binding to VH and Fc, is one of the best characterized. Staphylococcal protein A is frequently used in many different applications, such as affinity chromatography, where its ability to bind antibodies is utilized. The protein is both used for purification of IgG molecules and as affinity tag for protein purification. The five homologous domains, EDABC, that constitute protein A, each consists of approximately 58 aa, and share the Ig-binding feature (Uhlén, Guss et al. 1984). NMR analysis of the structure of the B domain shows a three-helix bundle with the helices ordered in an anti-parallel fashion. The domains of protein A exhibit binding both to the Fc and the Fab regions of immunoglobulins. By X-ray crystallography the structure of the B domain in complex with the Fc region of IgG has been solved, and it revealed an interaction that mostly involved amino acids of hydrophobic character (Deisenhofer 1981). Binding seems to occur in the interface between CH2 and CH3 of IgG, where 11 residues from helix 1 and helix 2 of the B domain are suggested to participate (Deisenhofer 1981; Gouda, Shiraishi et al. 1997; Gouda, Shiraishi et al. 1998). Also, the structure of the interaction between protein A and the Fab region has been solved. The crystal structure of the D domain binding the Fab region of human IgM disclosed the involvement of 11 residues of helices 2 and 3 from the D domain, and an interaction of a polar character with the variable heavy chain (Graille, Stura et al. 2000). By altering two positions in the B-domain of protein A an engineered variant called the Z domain has been made. In the N-terminal of the Z domain an alanine residue was replaced by valine. A glycine-to-alanine substitution was made for the removal of a hydroxylamine cleavage site (Nilsson, Moks et al. 1987), which also resulted in loss of binding to the Fab region (Jansson, Uhlén et al. 1998; Graille, Stura et al. 2000). The Z domain is small (6.7 kDa), easy to produce, has a stable three dimensional structure and also the capacity to refold (Ståhl and Nygren 1997). It has earlier been proven to be suitable for chemical peptide synthesis and thereby the introduction of synthetic active groups has been possible, extending the usability of the domain (Engfeldt, Renberg et al. 2005).

Benzoylphenylalanine (BPA) is a synthetic amino acid that can be incorporated in a peptide during synthesis. Benzophenone (BP), which is part of BPA, is a photoreactive group that forms covalent bonds to other amino acids upon UV-exposure. BPA is considered to be efficient, stable and also easy to handle (Dorman and Prestwich 2000) and it is primarily used when mapping protein-ligand interactions. When mapping interactions the strategy is to produce variants of a protein with BPA incorporated at different positions, and then allow the protein to bind its interaction partner (Kawamura, Hindi et al. 2008). When subjecting the complex to UV light BPA forms a diradical, which renders the generation of a covalent bond between the protein and its interaction partner possible.

SUMMARY OF THE INVENTION

The present invention provides a stringent and effective method for specific covalent labeling of immunoglobulins. By the use of a synthetic Z domain with the photoreactive probe BPA incorporated in the amino acid sequence, covalent conjugation to the antibody has been achieved. By combining the inherent affinity of the Z domain and the Fc-fragment with the ability of BPA to create a covalent bond, specifically labeled antibodies were achieved, characterized and tested in different platforms.

In a first aspect, the invention relates to a method for labeling antibodies and/or fragments thereof, comprising a) providing an IgG binding protein, which comprises α-helix structures, with a photoactivatable group and at least one label; b) forming a mixture of said IgG binding protein and the antibodies and/or fragments to be labeled; and c) UV illuminating said mixture for site-specific labeling of said antibodies and/or fragments thereof.

Preferably, the IgG binding protein is Protein A or a Protein A domain. Most preferably, the Protein A domain is the Z domain or variants thereof.

The IgG binding protein preferably comprises an amino acid substitution in a position in the vicinity of the IgG-binding surface.

The photoactivatable group is preferably selected from benzophenone (BP) which is part of benzoylphenylalanine; tetrafluorophenyl azide; trifluoromethylphenyl diazirine or 4-azidophenyl.

A preferred Z domain comprises SEQ ID NO 1 in which Phe in position 5 has been exchanged for BPA.

The label is preferably selected from: a fluorescent compound, a member of an affinity pair, DNA, PNA or radio isotopes. The label may be coupled to the IgG-binding protein via a linker such as PEG (polyethylene glycol).

In one embodiment of the invention, the Z domain is labeled in position 58 of SEQ ID NO 1. The labeling may be anywhere in the Z domain not affecting the activity of the protein. Preferably lysins in helix 3 and/or positions in the N-terminal are labeled. The B domain may also be substituted in the positions 21, 22, 23 and/or 39. Preferably the label is in position 58 and in position 39. Position 58 contains a naturally occurring lysine and position 39 a naturally occurring serine, which is converted to lysine before substitution. The label, such as biotin or biotin-PEG, binds via its carboxyl group to the amine group of the side chain of lysine.

In a second aspect, the invention relates to antibodies and/or fragments labelled according to the above method.

In a third aspect, the invention relates to use of the labeled antibodies or fragments for detection of molecules, such as proteins, antigens, antibodies.

The molecules may be present on or bound to a solid phase and be detected by Western blotting, ELISA or any other imaging technique. For example, antigens in tissue sample may be analysed using the antibodies and/or fragments of the invention.

The antibodies and/or fragments may also be used for detection of molecules in solution, wherein the antibodies or fragments are coupled to a solid phase, such as chromatography beads, magnetic beads, microtiter plate or sensor chip. The antibodies and/or fragments are coupled to the solid phase in an oriented way to maximize antigen binding.

DESCRIPTION OF THE DRAWINGS

FIG. 1: Mass spectrometry analysis of the synthetic Z domains.

A) The mass spectrum of Z5BPA-bio showing a molecular weight of 6981 Da (theoretical molecular weight: 6984 Da).

B) The mass spectrum of Z18BPA-bio showing a molecular weight of 6991 Da (theoretical molecular weight: 6994 Da).

FIG. 2: Covalent conjugation of the Z-variants was evaluated by using the Luminex platform. A) The two different strategies used for analysis of covalent coupling are shown.

B) The cross-linking of Z5BPA-bio and Z18BPA-bio. As negative control uncoupled beads were used. Strategy 1 in FIG. 2A was used. Mean value of two different experiments is shown.

C) The efficiency of covalent linking when using Z5BPA-bio was evaluated. To assess the level of covalently linked Z domains a reference sample was treated with low pH to release unlinked domains. As reference unmodified Z was used. Uncoupled beads were used as negative control. Strategy 2 in FIG. 2A was used. Mean value of three different analyses for the samples treated with low pH is shown.

Figure 3:
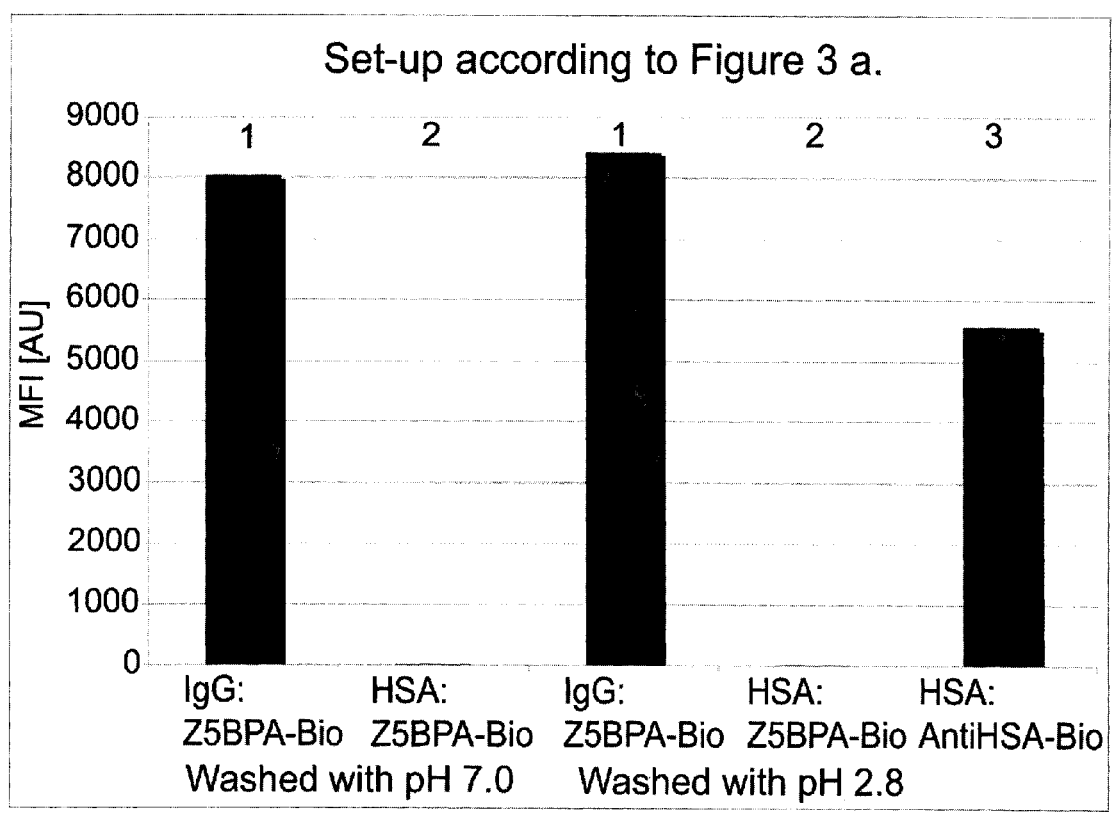

FIG. 3: The degree of covalently linked Z5BPA-bio domain in a complex sample was analyzed.

A) The three different strategies used for analysis of covalent coupling are shown.

B) The degree of cross-linking was analyzed both with and without HSA in the sample. Covalent linking of Z5BPA-bio was unaffected of the HSA present in the sample. Set up according to strategy 1 in FIG. 3A was used.

C) To assess if Z5BPA-bio was able to covalently bind to the HSA molecule, a Western blot was performed. In the left panel the number of covalently linked Z5BPA-bio in three different samples was analyzed using streptavidin-HPR. No attachment to the HSA molecule could be detected. In the right panel the presence of HSA in the samples was analyzed by using HPR-conjugated antibodies targeting HSA.

D) To confirm the conclusion from the previous experiment a Luminex experiment was made where both the amount of biotinylated IgG molecules and HSA molecules were analyzed using strategy number 1 in FIG. 3A. The number of biotinylated IgG molecules was shown to be high, both after and before treatment with low pH. This indicates a high degree of covalent coupling by Z5BPA-bio. The amount biotinylated HSA-molecules was analyzed using strategy number 2 in FIG. 3A. No biotinylation could be detected before or after treatment with low pH. To ensure the presence of HSA a third strategy was used (number 3 in FIG. 3A), hence, detecting HSA with an HSA-binding antibody and thereby the presence of HSA was confirmed.

Figure 4:
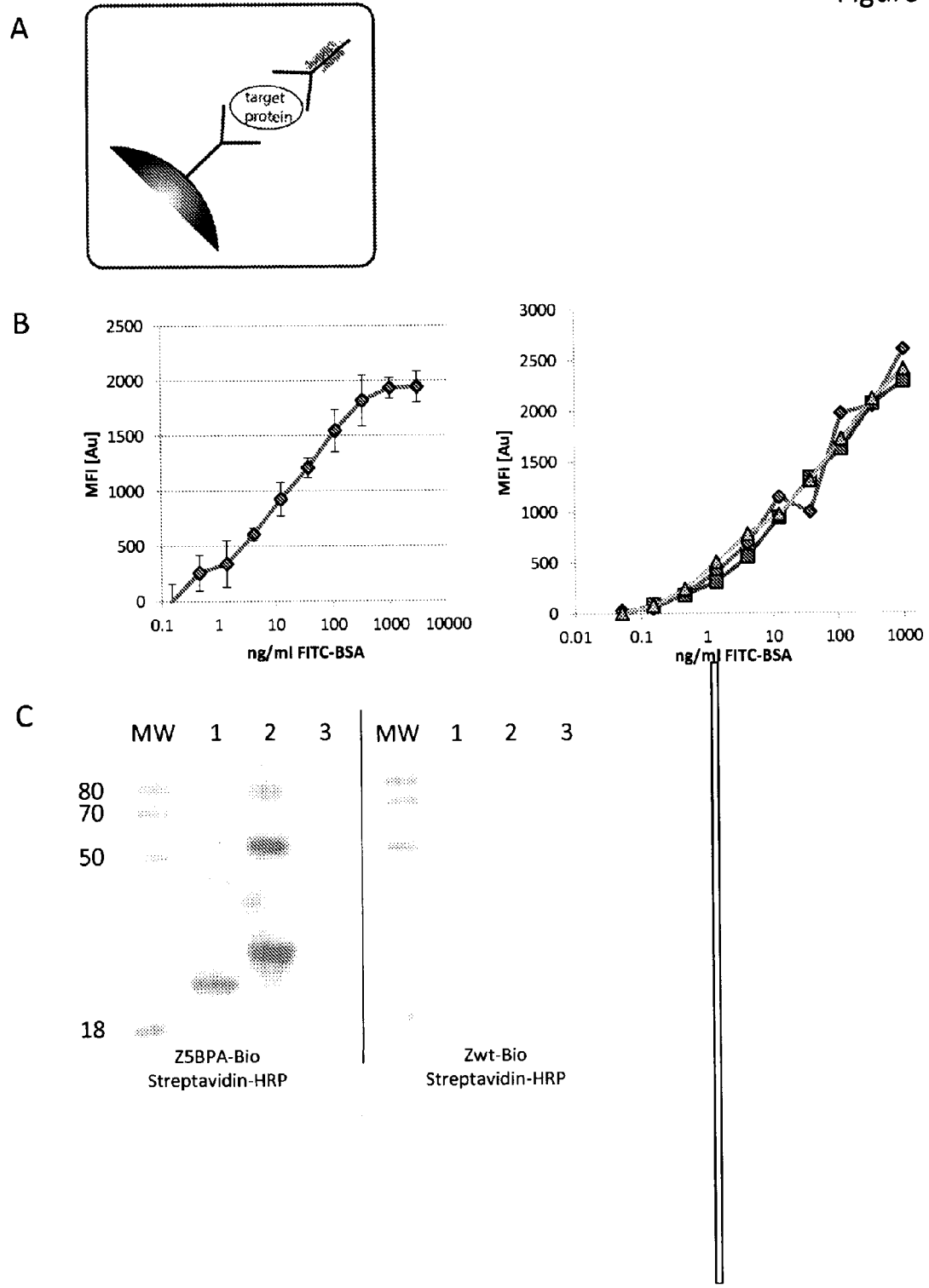

FIG. 4: The covalently cross-linked antibodies were used in two different commonly used assays.

A) A sandwich analysis where the capturing antibodies were attached to Luminex beads was made.

B) Incubation of the beads with different concentrations of antigen and subsequent washing was performed. The amount of captured antigen was analyzed by using detection antibodies covalently linked to Z5BPA-bio combination with streptavidin-R-phycoerythrin. The diagram to the left shows human monoclonal IgG1 targeting FITC-BSA and in the right diagram mouse monoclonal IgG2a is used.

C) Covalently cross-linked antibodies were used in a Western blot analysis. In the left panel detection was made by using an antibody covalently linked to Z5BPA-bio and in the right panel the same antibody but with Zwt-bio was used as control. Protein samples on the gel are: MW, a molecular weight marker; lane 1, His$_6$ABP (19 kDa); lane 2, His$_6$ABP-PrEST (25.5 kDa).

DETAILED DESCRIPTION OF THE INVENTION

Material and Methods
General

Recombinantly produced Zwt, was used as a reference in several experiments (Nilsson, Moks et al. 1987). The protein domain was randomly biotinylated resulting in an average of four biotin moieties/domain, as measured by MALDI-MS (data not shown). Antibodies were from different suppliers;, anti FITC-BSA (human IgG1 and mouse IgG2a, BioInvent International AB, Lund, Sweden) and anti $His_6$-ABP (polyclonal, Atlas Antibodies AB, Stockholm, Sweden).

Production of Peptides
Materials

The solvents N,N-dimethylformamide (DMF) and dichloromethane (DCM), and the Fmoc-protected amino acids; Fmoc-Val-OH, Fmoc-Glu(OtBu)-OH, Fmoc-Ala-OH, Fmoc-Phe-OH, Fmoc-Ile-OH, Fmoc-His(Trt), Fmoc-Pro-OH, were obtained from Applied Biosystems (Foster City, Calif., USA). Amino acids; Fmoc-Asn(Trt)-OH, Fmoc-Lys (Boc)-OH, Fmoc-Lys(Mtt)-OH, Fmoc-Gln(Trt)-OH, Fmoc-Leu-OH and Boc-Val-OH were purchased from NovaBiochem (Darmstadt, Germany) and remaining amino acids; Fmoc-Tyr(tBu)-OH, Fmoc-Ser(tBu)-OH, Fmoc-L-Arg(Pbf)-OH and Fmoc-Asp(OtBU)-OH from PerSeptive Biosystems (Warrington, UK). 2-(1H-Benzotriazole-1-yl)-1,1,3,3-tetramethyluronium hexafluorophosphate (HBTU) and 1-hydroxybenzotriazole (HOBt) were purchased from Iris Biotech GmbH (Marktredwitz, Germany).Acetic anhydride ($Ac_2O$), piperidine and N,N-diisopropylethylamine (DIEA) were obtained from Alfa Aesar (Karlsrue, Germany). The photoactivable amino acid Fmoc-L-4-benzoylphenylalanine (Fmoc-BPA-OH) was acquired from Peptech Corporation (Burlington, Mass., USA). D-biotin was purchased from SIGMA (St. Louis, Mo., USA), trifluoroacetic acid (TFA) from Fluka (St. Louis, Mo., USA), triisopropylsilane (TIS) from Aldrich (St. Louis, Mo., USA), ethanol from Solveco (Rosersberg, Sweden) and acetonitrile were obtained from MERCK (Whitehouse Station, N.J., USA). Both N-methylpyrrolidone (NMP) and tert-butyl methyl ether were purchased from VWR (Arlington Heights, Ill., USA).

Synthesis

The two variants ZF5BPA (Z5BPA) and ZH18BPA (Z18BPA) were produced by solid phase peptide synthesis (SPPS) using Fmoc/tBu protection strategy.

dine in NMP for 10 min. Coupling of amino acids were performed with a ten-fold molar excess for 10-11.5 min. Apart from the amino acids underlined in table 1, single couplings were carried out, and activation of amino acids was executed with HOBt (1 eq) and HBTU (1 eq) in DMF and DIEA (2 eq) in NMP. For the procedure of capping of unreacted amino acids in the peptide, the peptide-resin was subjected to a solution containing a molar excess of $Ac_2O$, HOBt and DIEA for 5 min. Both peptides, Z5BPA and Z18BPA, were assembled with amino acids protected with standard side-chain protecting groups except in position 58 where Fmoc-Lys(Mtt) was introduced. The photactivable probe Fmoc-BPA-OH was incorporated in position 5 in Z5BPA and in position 18 in Z18BPA. Boc-Val-OH was used in position 1 in the synthesis of the peptide Z18BPA.

Modification and Processing of Peptides

Incorporation of biotin in the side-chain of position 58 in Z5BPA and Z18BPA was performed with the peptides still bound to the resin. The peptide-resin was repeatedly (10×2 min) treated with TFA/TIS/DCM (1:5:94) for the removal of the 4-methyltrityl (Mtt) group protecting the $\epsilon$-amine of Lys58. Biotin was coupled with D-biotin (5 eq), HOBt (5 eq), HBTU (5 eq) and DIEA (10 eq) in NMP for 2×1 h. Throughout the manual modification of the peptide-resin, the reactions were monitored using Kaiser test (Kaiser, Colescott et al. 1970). The Fmoc-group on Z5BPA was cleaved off manually by subjecting it to 20% piperidine-NMP for 10 min.

The release of Z5BPA and Z18BPA from the resin and the removal of protecting groups were achieved through subjecting the peptide-resin to a solution of TFA/TIS/$H_2O$ (95:2.5:2.5) for 2 h in room temperature. Thereafter extraction of the peptides in $H_2O$/tert-butyl methyl ether (1:1) was repeated 3 times before filtration and lyophilization of the aqueous phase.

HPLC and MS

For purification and analysis of products from the syntheses of Z5BPA and Z18BPA before and after biotinylation RP-HPLC was employed. RP-HPLC was performed using a Silica-C18 column with 3.5 μm particle size and 4.6×150 mm length (Agilent Technologies). During analytical conditions a gradient of 20-60% B (A: 0.1 TFA/$H_2O$; B: 0.1% TFA/$CH_3CN$ over 25 min at 0.9 mL/min flow rate was used. Using the same column and flow rate the peptides were purified, applying a 25 min gradient of 28-38% B for the preparation of Z5BPA-biotin (Z5BPA-bio), and a 25 min gradient of

TABLE 1

Amino acid sequences of Z5BPA and Z18BPA.

ZF5BPA (denoted Z5BPA)
VE<u>NKXN</u>KE<u>QQ</u>NAFYEILHLP<u>NL</u>NEE<u>QRN</u>AFIQSLKDDPSQSANLLAEAKKLNDAQAPK$^{Mtt}$ ZH18BPA (denoted Z18BPA)
VE<u>NKFN</u>KE<u>QQ</u>NAFYEIL<u>XL</u>P<u>NL</u>NEE<u>QRN</u>AFIQSLKDDPSQSANLLAEAKKLNDAQAPK$^{Mtt}$ Underlined amino acids were coupled twice during synthesis.
X = benzoylphenylalanine.

Z5BPA and Z18BPA correspond to SEQ ID NO 1 and 2, respectively, in the Sequence Listing.

Synthesis was performed on a 433 A Peptide synthesizer (Applied Biosystems, Foster City, Calif.), and the protocol used was based on the FastMoc0.1ΩMonPrevPk chemistry file of the SynthAssist 2.0 software package (Applied Biosystems). Both syntheses were performed using acid-labile Fmoc-amide resin (substitution 0.67 mmol/g, Applied Biosystems), and a 0.1 mmole scale. Cleavage of the Fmoc group throughout the synthesis was performed using 20% piperi- 30-40% B for Z18BPA-biotin (Z18BPA-bio). Fractions obtained from RP-HPLC were analyzed by MS and after verification of the correct products samples were pooled and lyophilized. The protein concentration of the samples was determined by amino acid analysis (Aminosyraanalyscentralen, Uppsala, Sweden).

Mass spectrometry was used to verify that correct products were obtained. The products from the syntheses of Z5BPA and Z18BPA were analyzed by ESI-MS, performed on a Q-TOF II (Waters corporation, Micromass MS Technologies). The HPLC eluate containing approximately 30% of $CH_3CN$ was diluted 1:5 with a solution of 5% $CH_3CN$ and 0.1% formic acid (MERCK), and as reference myoglobin was used. For Z5BPA-bio and Z18BPA-bio the fractions collected in RP-HPLC were analyzed using a MALDI-MS Biflex IV (BRUKER Daltonics Leipzig, Germany). The eluate from HPLC was mixed 1:1 with a saturated solution of sinapaic acid (SA) (Fluka), and put on a MALDI target for analysis. As reference and for external calibration myoglobin, carbonic anhydrase II (CA II) and insulin (all obtained from Sigma-Aldrich), were used.

Biacore Analysis

Analysis of the binding kinetics of Z5BPA and Z18BPA to different IgG molecules was performed by the use of SPR technology (BIAcore 2000 instrument, Biacore, Uppsala, Sweden). Antibodies and human serum albumin (HSA) were diluted to 10 µg/ml in 10 mM NaAc pH 5.5 for immobilization onto a CM5 sensor chip. The proteins were immobilized on the sensor surface giving approximately 2,000 response units (RU) for the antibodies, and 700 RU for HSA. During analysis of Z5BPA and Z18BPA binding to immobilized antibodies a flow rate of 30 µl/min at 25° C. were used. HBS-EP (HEPES 100 mM, NaCl 1.5 M, EDTA 34 mM (Merck) and 0.05% Tween (VWR) was used as a running buffer, and for regeneration of surfaces 10 mM HCl. Samples of Z5BPA-bio in concentrations 1.6 nM, 3.2 nM, 6.4 nM, 12.7 nM, 25.4 nM, 50.9 nM, 101.8 nM and 203.5 nM were used. Concentrations of Z18BPA-bio used in Biacore were 11.9 nM, 23.8 nM, 47.5 nM, 95.0 nM, 190.0 nM, 380 nM, 760 nM and 1560 nM. Biacore analysis were also made on Zwt 5.0 nM, 9.9 nM, 19.8 nM 39.7 nM, 79.4 nM, 158.8 nM, 317.5 nM and 635 nM. All samples were run in duplicates. The software BIAevaluation 3.2 (BIAcore AB) was employed to determine the dissociation constants based on the Langmuir 1:1 model.

General Procedure for Photoconjugation

The antibodies were diluted in PBST to a concentration of 100 nM and mixed with a ten-fold molar excess of Z5BPA-bio or Z18BPA-bio. Incubation of the mixture of antibodies and Z5BPA-bio or Z18BPA-bio was performed in room temperature with mixing for 1 h. Cross-linking of the antibody and the Z-biotin variants was achieved by subjecting the mixtures to UV light (365 nm Spectroline BLE-8T365 from Spectronics Corporation) for 1 h on ice in a Ultraviolet Crosslinker (Amersham Life Science, Uppsala, Sweden).

Photoconjugation of antibodies was also performed with HSA in the solution (Albumina Kabi). The antibody solution was supplemented with HSA to a concentration of 800 nM in PBST. All other parameters were kept constant when subjecting the sample to the cross linking procedure.

For buffer exchange spin concentrators with a 10-kDa cut-off (Vivaspin 500 membrane 10 000 MWCO PES, Sartorius Stedim Biotech) were used according to the manufacturer's recommendations (centrifugation at 15,000 rcf for 10 min). Exchange of buffer was repeated several times, using 0.2 M HAc (VWR), pH 3.3, for lowering the pH and PBST for restoring the pH to 7. Photoconjugated antibodies were recovered from the concentrators and a spectrometric analysis of the protein content was performed (280 nm, $\epsilon$=210 00 $M^{-1}$ $cm^{-1}$, Eppendorf BioPhotometer).

Luminex
Bead Coupling

Proteins and antibodies were coupled to carboxyl groups on beads with different bead id:s according to the manufacturer's recommendation (COOH Microspheres, Luminex Corp.). The amount of either 1.6 µg anti-FITC-BSA or 3.2 µg anti-Apolipoprotein B was used for coupling to approximately $5*10^5$ beads. Protein FITC-BSA (BioInvent International AB, Lund, Sweden) and $His_6$-ABP (Atlas Antibodies AB, Stockholm, Sweden) were coupled using 2 µg for approximately $2.5*10^5$ beads and 10 µg for $1*10^6$ beads respectively. Coupled beads were kept at 4° C. in a storage buffer (Blocking Reagent for ELISA, Roche Applied Science). Before use, all coupled beads were sonicated for 5 min with an ultrasonic device (Branson Ultrasonic Corp).

Analysis of Photoconjugated Antibodies

Antibodies subjected to photoconjugation were diluted with PBST to a concentration of 100 nM (15 µg/ml). Filter plates (0.45 µm MSHVN45 MultiScreen® HTS, HV Millipore) were used for incubation of 45 µl diluted antibody with 5 µl bead solution (200 beads/µl) at 23° C. with mixing for 1 h. Washing with 3×50 µl PBST was performed before antibodies and beads were supplied with PhycoLink® Streptavidin-R-Phycoerythrin (HB) (Prozyme, San Leandro, USA) diluted to 2.2 µg/ml. The samples were incubated at 23° C. for 20 min, washed with 3×50 µl PBST and finally supplied with 150 µl PBST prior to measurement in Luminex Lx200. When performing the sandwich assay the first incubation with beads was made with target protein at 23° C. with permanent mixing for 1 h, thereafter a wash step (3×50 µl PBST) was introduced, followed by incubation of antibodies, according to the procedure described above.

Western Blot

Western blot was performed by running 2 µg of protein ($His_6$ABP, $His_6$ABP-PrEST and HSA) on NuPAGE 4-12% Bis-Tris SDS-PAGE gradient gels and 2 µg of antibodies (IgG, IgG+HSA, HSA) on NuPAGE 3-8% Tris-Acetate SDS-PAGE gradient gels (Invitrogen, Carlsbad, Calif., USA) under reducing conditions, followed by transfer to PVDF membranes (Invitrogen) according to the manufacturer's recommendations. Membranes were soaked in methanol and blocked (0.5% casein, 0.5% Tween20, 1× PBS; 8 mM $Na_2HPO_4$, 2 mM $NaH_2PO_4$, 0,15 M NaCl) for 1 h at room temperature during constant shaking. The membranes with proteins ($His_6$ABP, $His_6$ABP-PrEST and HSA) were then incubated with photoconjugated anti-HisABP or anti-HisABP treated with Zwt-biotin (15 nM) for 1 h, followed by washing (1× PBST) and incubation with peroxidase-conjugated streptavidin (diluted 1:5000, DakoCytomation, Glostrup, Denmark). The membranes with transferred antibodies were incubated with peroxidase-conjugated streptavidin (diluted 1:5000) or first goat anti-human albumin (diluted 1:1000, Bethyl, Montgomery, Tex., USA) for 1 h, then secondly incubated with peroxidase-conjugated anti-goat IgG (diluted 1:100 000, Sigma-Aldrich), followed by washing (1× PBST) Detection was carried out using a CCD-camera (Bio-Rad Laboratories) with Immobilion Western Chemiluminescent HRP substrate (Millipore, Billerica, Mass., USA) according to the manufacturer's protocol.

Results
Design and Synthesis of Z-Variants

The procedure of labeling and covalent attachment of reporter groups to antibodies is traditionally done through the chemistry of amine- or carboxyl-groups in the antibody. This can be an efficient method but since the labeling occurs randomly, many different groups in the protein have the possibility to react and the conjugated group might influence the binding of the antibody to its antigen. Hence, an optimization of the labeling conditions is a necessity for every antibody and therefore specific and directed labeling would be beneficial for many applications. The present invention provides a novel method that enables a specific labeling of antibodies where a photoactivable probe together with a specific binding event is utilized to achieve covalent and specific attachment to immunoglobulins. To achieve a specific and reliable covalent labeling, the IgG-binding domain Z was utilized.

After studying the available structural data of Protein A (domain B) and its interaction surface with IgG, the positions Phe5 and His18 were chosen to be exchanged for BPA. Phenylalanine 5 is positioned in the N-terminal part of the domain, close to the first helix, and it is also claimed to participate in the binding between the B-domain and IgG (Deisenhofer 1981). The other position, histidine 18, is the last amino acid in the first helix and it is not suggested to be part of the binding to IgG, but is situated in close proximity to the binding surface. Hence, two variants of the Z domain were produced, Z5BPA and Z18BPA. To achieve specific incorporation of the photoreactive probe the two molecules were produced using solid phase peptide synthesis. In table 1 the sequences of the synthesized molecules are shown, where underlined amino acids were coupled twice during synthesis to ensure a high yield of the product. In both Z5BPA-bio and Z18BPA-bio a D2E substitution was made to avoid aspartimide formation during synthesis. This substitution has earlier been shown not to interfere with the structural or functional behavior of the Z domain (Engfeldt, Renberg et al. 2005).

The synthesis products, ZF5PBA and Z18BPA, were purified using RP-HPLC, and the purified correct products were verified using MS (data not shown). To enable easy and flexible detection and to be able to analyze the efficiency of the conjugation the two variants were specifically biotinylated in the C-terminus of the protein domain. This was made by applying an orthogonal strategy, through the incorporation of a lysine protected with a 4-methyltrityl (Mtt) group in the last position in the sequence of the domains. Also these protein products were successfully purified to homogeneity and analyzed by MS (FIGS. 1a and b).

Analysis of the Binding Characteristics of the Z-Variants

The ability of the Z domain to refold after synthesis has been shown previously (Engfeldt, Renberg et al. 2005), and therefore retained binding to IgG was expected. However with the introduction of BPA in different positions in the proximity of or in the binding surface there is a potential risk of influencing the ability to bind IgG. Therefore an analysis of the binding kinetics of the two Z variants using surface plasmon resonance (SPR) was made. The ability of the two novel Z variants to bind to different IgG molecules was analyzed and compared to the parental Z domain. The analysis revealed an affinity of Z5BPA-Bio to IgG comparable to the parental Z. However, a considerably lower affinity was detected when analyzing the binding of Z18BPA-Bio to IgG (Table 2).

TABLE 2

Kd values for Z5BPA-bio, Zwt and Z18BPA-bio binding to human IgG1 and mouse IgG2a

|  | Z5BPA-bio | Z18BPA-bio | Zwt |
| --- | --- | --- | --- |
| Human IgG1 | 10 nM | 60 µM | 20 nM |
| Mouse IgG2a | 650 nM | — | 550 nM |
| Rabbit IgG poly | 30 nM | — | 60 nM |

Evaluation of Covalent Coupling of Z-Variants to Immunoglobulins

Two approaches were employed in order to evaluate covalent coupling of the two modified Z domains to IgG. In the first approach polyclonal rabbit IgG was coupled to Luminex beads and then incubated with the synthetic Z domains, followed by light-induced activation of the covalent coupling (FIG. 2a, setup 1). By using this approach we were able to show that Z5BPA-bio could be covalently attached to IgG.

Also, data show that the variant Z18BPA-bio was not covalently linked to IgG by this treatment (FIG. 2b). To ensure that this behavior was not concentration-dependent, a higher concentration of Z18BPA-bio was used, but still no covalent coupling was obtained (data not shown).

The successful conjugation of Z5BPA-bio to IgG was further confirmed in the second approach, where cross-linking was performed in solution and the photo-conjugated antibodies were evaluated in the Luminex system. In this experiment, Z5BPA-bio and IgG were incubated in solution and subjected to UV light for cross-linking. To remove excess of unbound Z molecules a spin filter column (10 kDa cut-off) was used. This also allows for buffer exchange and lowering of pH, which enable release of non-covalently bound Z molecules from IgG. Hence, the bound and cross-linked Z domains will stay attached to the IgG molecules while non-covalently bound Z domains will be released and washed away. In order to investigate the efficiency of covalent coupling of the bound Z5BPA-bio to the antibody, a sample of the photo-conjugated antibodies was taken out before lowering of pH. Also, as negative control, recombinantly produced and biotinylated Z was used. For the evaluation of the conjugation, antigens were covalently linked to Luminex beads and subsequently incubated with corresponding IgG molecules from the conjugation experiment (FIG. 2a, setup 2). As can be seen in FIG. 2c, for the negative control, biotinylated Z, the signal diminishes when lowering the pH, hence the non-covalent interaction between Z and IgG is possible to break with low pH. Moreover, the Z5BPA-bio is efficiently linked to the IgG molecules since the IgG molecules after treatment with low pH still give a strong signal. Also, the ability to bind the antigen indicates that the paratope of the antibody is intact. Evaluation of the conjugation efficacy was made by comparing the achieved signal before and after treatment with low pH. Thereby the conclusion that more than 80% of the bound Z-molecules were efficiently cross linked to the immunoglobulins could be drawn (FIG. 2c).

Specificity of Labeling

Since many manufactured antibodies are stabilized by the addition of other proteins, commonly albumin, it is important to be able to perform the conjugation in complex solutions. To investigate the selectivity of the labeling, a solution containing eight times more HSA than specific monoclonal antibodies was prepared. The efficiency of the conjugation was analyzed and compared with conjugation without HSA (assay number 1 in FIG. 3a). As can be seen in FIG. 3b the efficiency of the labeling is not affected by the presence of HSA. To assess any unwanted biotinylation of HSA, a Western blot experiment was performed. In the first experiment all biotinylated proteins were detected (FIG. 3c, left panel) and in the second setup, the present HSA molecules were detected (FIG. 3c, right panel). This experiment indicates that no covalent coupling of the biotinylated Z-domains to HSA has occurred. However, since the migration of HSA and the heavy chain of IgG in complex with the Z domain in an SDS-PAGE is rather similar, another experiment was performed where the biotinylation was assessed using Luminex analysis. An HSA-binding protein or an antigen was covalently attached to Luminex beads, respectively. Thereafter, the UV-exposed IgG/HSA mixture was mixed with beads, either with the ability to bind HSA or conjugated with antigen. Thereafter biotinylation was assessed through fluorescently labeled streptavidin. The conclusion that no biotinylation of HSA was obtained could be drawn since no signal from fluorescently labeled streptavidin mixed with the HSA-binding beads was detected (assay number 2 in FIG. 3a). However, the ability of HSA to bind to the beads was confirmed by HSA-recognizing antibodies conjugated with biotin (setup 3 in FIG. 3a, FIG. 3d). In parallel, from the same conjugation experiment, high signals from the present IgG-molecules were observed since these were able to selectively bind to the antigen-conjugated beads (assay number 1 in FIG. 3a). Here, high signals were detected both before and after washing with low pH, showing specific covalent conjugation.

Use of Conjugated Antibodies

The photoconjugated antibodies were used in a sandwich assay set-up where capture antibodies were coupled to beads and incubated with target protein in various concentrations (FIG. 4A). After thorough washing, target-specific photoconjugated antibodies were added. The beads were washed and the fluorescence from streptavidin-R-phycoerythrin was detected by using the Luminex platform. Analyses using both human monoclonal antibodies and mouse monoclonal antibodies recognizing FITC-BSA were successfully performed. As can be seen in FIG. 4, the antigen could be detected down to a concentration of 0.1 ng/ml within a concentration window spanning 4 orders of magnitude.

Also, the conjugated antibodies were used for detection in a Western blot assay. By conjugation of the antibodies with Z5BPA-bio the protein targeted by the antibodies could be detected by streptavidin-HRP. In FIG. 4c, two Western blot membranes are shown. On the rightmost membrane, proteins are detected with conjugated antibodies and on the left membranes unconjugated antibodies are used. The molecular weights of the protein bands detected are as expected, hence the system works both in a sandwich set-up with the antigen in solution and in detection of proteins in bound to a membrane.

Discussion

Both suggested Z variants were successfully synthesized with high yield and the C-terminal biotinylation was efficiently and specifically made through an orthogonal protection strategy (FIG. 1). The interaction between IgG and the two synthesized Z variants was analyzed revealing a retained affinity for the Z5BPA-bio molecule while Z18BPA-bio showed very low affinity ($\approx$100 μM, Table 2)). For the Z5BPA-bio molecule both on- and off-rate are in the same ranges as for the parental Z domain (data not shown). The retained affinity of the Z5BPA-bio variant could be due to the steric similarity of phenylalanine and BPA making the inherent structure of Z intact. The addition of the extra benzoyl group seems to fit well between the two molecules upon binding. On the other hand, replacement of the histidine 18 for BPA is deleterious and destroys the interaction with IgG. This could be due to the change of charge in the position of amino acid 18. Also the larger side group of the unnatural amino acid could stericallly inhibit the ability to bind IgG. This photoactivable molecule has earlier been used to covalently label antibodies through incorporation in an antibody binding molecule from protein G (Jung, Lee et al. 2009), but a different strategy for production of the binding domain was used. In this publication they have recombinantely produced the IgG-binding domain and after purification covalently attached a BPA-group via a cysteine. Moreover, the area of application in the referred study was to covalently attach the antibodies on a solid support in an oriented way. In this invention we have focused on labeling of the antibodies for detection purposes.

A very important characteristic of a molecule used for selective labeling is the efficiency of the covalent linking. Hence, a thorough characterization of this was performed. Different IgG molecules were used for this analysis and a difference in efficiency could be found. Although all immunoglobulins with affinity for Z covalently labeled efficiently (more than 80%, FIG. 2) some differences between the subclasses could be detected. The earlier study by Jung et al (Jung, Lee et al. 2009) reports 50% efficacy in the coupling step.

When using the coupling strategy in complex solution we could conclude that no unwanted linking could be detected, despite high concentration of both HSA and Z5BPA-bio (FIG. 3). This is of outermost importance and shows that the benzophenone (BP) group needs to be in close proximity to create a covalent link. Also specific and stable interaction as well as UV light of correct wavelength is needed. The necessity of UV light makes this photoactivable probe convenient and easy to handle since no light protection is needed during the synthesis, purification or other experimental steps where no conjugation is desired.

To assess the functionality of the covalently linked antibodies two different methods were used. A sandwich assay was successfully made by taking advantage of capturing antibodies covalently linked to Luminex beads. The prepared beads were incubated with different concentrations of antigen (FIG. 4A). Hence detection could be made by streptavidin using conjugated antibodies both from mouse and human. Also an ordinary Western blot was made showing that also here the conjugated antibodies successfully detect the anticipated proteins on the membrane. These data show that the covalent linkage between IgG and Z5BPA-bio is stable and usable in different well-known assays. When performing the sandwich assay antigen concentrations down to 0.1 ng/ml could be detected. When conjugating the antibodies in this study we have been able to reach 1-2 biotin on each antibody since only one biotin is incorporated in each Z domain. By replacing Ser 39 with Lys and introducing PEG-conjugated biotin at this position as well as position 58, we obtained a Luminex signal that was nearly 100% higher than labeling with only one biotin.

Here we have presented a stringent and effective method for labeling of antibodies by utilizing an IgG binding protein domain, Z. By, during synthesis, introducing a photoactivable group in the protein scaffold, a covalent linkage between IgG and the synthesized protein domain can be created. This linkage has been shown to be efficiently formed and stable in different conditions. Here we have been using biotin as the reporting group but a large variety of different groups could be introduced in the protein domain to tailor made the antibodies for a certain purpose. The new approach for labeling of antibodies presented here is both flexible and reliable and would be suitable for a wide range of applications where antibodies are used in the detection step.

REFERENCES

Deisenhofer, J. (1981). "Crystallographic refinement and atomic models of a human Fc fragment and its complex with fragment B of protein A from *staphylococcus aureus* at 2.9- and 2.8-Å resolution." *Biochemistry* 20: 2361-2370.

Dorman, G. and G. D. Prestwich (2000). "Using photolabile ligands in drug discovery and development." *Trends Biotechnol* 18(2): 64-77.

Engfeldt, T., B. Renberg, et al. (2005). "Chemical synthesis of triple-labelled three-helix bundle binding proteins for specific fluorescent detection of unlabelled protein." *Chembiochem* 6(6): 1043-50.

Gouda, H., M. Shiraishi, et al. (1997). "NMR Study of the Interaction between the B Domain of Staphylococcal Protein A and the Fc Portion of Immunoglobulin G." *Biochemistry* 37: 129-136.

Gouda, H., M. Shiraishi, et al. (1998). "NMR study of the interaction between the B domain of staphylococcal protein A and the Fc portion of immunoglobulin G." *Biochemistry* 37(1): 129-36.

Graille, M., E. A. Stura, et al. (2000). "Crystal stucture of a *Staphylococcus aureus* protein A domain complexed with the Fab fragment of a human IgM antibody: Structural basis for recognition of B-cell receptors and superantigen activity." *Proc. Natl. Acad. Sci.* 97: 5399-5404.

Jansson, B., M. Uhlén, et al. (1998). "All individual domains of staphylococcal protein A show Fab binding." *FEMS Imm Med. Microbiol.* 20: 69-78.

Jung, Y., J. M. Lee, et al. (2009). "Photoactivable antibody binding protein: site-selective and covalent coupling of antibody." *Anal Chem* 81(3): 936-42.

Kaiser, E., R. L. Colescott, et al. (1970). "Color test for detection of free terminal amino groups in the solid-phase synthesis of peptides." *Anal Biochem* 34(2): 595-8.

Kawamura, A., S. Hindi, et al. (2008). "Binding is not enough: flexibility is needed for photocrosslinking of Lck kinase by benzophenone photoligands." *Bioorg Med Chem* 16(19): 8824-9.

Nilsson, B., T. Moks, et al. (1987). "A synthetic IgG-binding domain based on staphylococcal protein A." *Protein Eng* 1(2): 107-13.

Ståhl, S. and P. A. Nygren (1997). "The use of gene fusions to protein A and protein G in immunology and biotechnology." *Pathol Biol (Paris)* 45(1): 66-76.

Uhlén, M., B. Guss, et al. (1984). "Complete sequence of the staphylococcal gene encoding protein A." *J. Biol. Chem.* 259: 1695-1702.

The invention claimed is:

1. A method for labeling antibody including fragments thereof, comprising:
   a) providing an IgG binding protein, which comprises α-helix structures, with a photoactivatable group and at least one label and providing antibody and/or fragment thereof to be labeled;
   b) forming a mixture of said IgG binding protein and the antibodies and/or fragments to be labeled; and
   c) UV illuminating said mixture for site-specific labeling of said antibody and/or fragments thereof;
   wherein the IgG binding protein is a Z domain of Protein A comprising SEQ ID NO 1 in which Phe in position 5 has been exchanged for BPA (benzoylphenylalanine).

2. The method of claim 1, wherein the photoactivatable group is selected from benzophenone which is part of benzoylphenylalanine; tetrafluorophenyl azide; trifluoromethylphenyl diazirine or 4-azidophenyl.

3. The method of claim 1, wherein the label is selected from the group consisting of a fluorescent compound, a member of an affinity pair, DNA, PNA, and a radioisotope.

4. The method of claim 1, wherein the Z domain is labeled in position 58 of SEQ ID NO 1.

5. The method of claim 4, wherein the Z domain is further labeled in position 39 of SEQ ID NO 1 by first replacing Ser with Lys.

6. The method of claim 1, wherein the label is conjugated to a linker.

7. The method of claim 5, wherein the label is biotin and the linker is PEG.

8. The method of claim 1, wherein the fragment is an Fc fragment and said Fc fragment is labelled.

9. Antibodies and/or fragments thereof labelled according to claim 1.

* * * * *